(12) United States Patent
Nishino et al.

(10) Patent No.: US 8,232,389 B2
(45) Date of Patent: Jul. 31, 2012

(54) METHOD FOR CRYSTALLIZATION OF AZETIDINONECARBOXYLIC ACID

(75) Inventors: Keita Nishino, Takasago (JP); Teruyoshi Koga, Takasago (JP); Masafumi Fukae, Takasago (JP); Yasuyoshi Ueda, Takasago (JP)

(73) Assignee: Kaneka Corporation, Osaka (JP)

( * ) Notice: Subject to any disclaimer, the term of this patent is extended or adjusted under 35 U.S.C. 154(b) by 414 days.

(21) Appl. No.: 12/308,413

(22) PCT Filed: Jun. 13, 2007

(86) PCT No.: PCT/JP2007/061937
§ 371 (c)(1),
(2), (4) Date: Dec. 15, 2008

(87) PCT Pub. No.: WO2007/145260
PCT Pub. Date: Dec. 21, 2007

(65) Prior Publication Data
US 2010/0298556 A1    Nov. 25, 2010

(30) Foreign Application Priority Data

Jun. 16, 2006 (JP) .................................. 2006-167410

(51) Int. Cl.
*C07F 7/18* (2006.01)
(52) U.S. Cl. ...................................................... 540/200
(58) Field of Classification Search .................... 540/200
See application file for complete search history.

(56) References Cited

U.S. PATENT DOCUMENTS

| | | | |
|---|---|---|---|
| 5,371,214 A | 12/1994 | Miura et al. | |
| 5,574,152 A | 11/1996 | Miura et al. | |
| 5,641,770 A * | 6/1997 | Kwak et al. | 514/210.12 |
| 5,792,861 A * | 8/1998 | Hara et al. | 540/200 |
| 6,340,751 B1 | 1/2002 | Saito et al. | |
| 6,858,727 B2 | 2/2005 | Lee et al. | |
| 2011/0144326 A1 * | 6/2011 | Tseng et al. | 540/200 |

FOREIGN PATENT DOCUMENTS

| | | |
|---|---|---|
| EP | 0 632 037 | 6/1994 |
| JP | 4-368365 | 12/1992 |
| JP | 5-105660 | 4/1993 |
| JP | 5-170733 | 7/1993 |
| JP | 7-25848 | 1/1995 |
| JP | 2000-44538 | 2/2000 |
| WO | 01/72704 | 10/2001 |
| WO | 02/12230 | 2/2002 |
| WO | 2004/103966 | 12/2004 |
| WO | 2006-028037 | 3/2006 |

OTHER PUBLICATIONS

Lu, Organic Process Research & Development (2001), 5(2), 186-188.*
Fuentes, Journal of Organic Chemistry (1987), 52(12), 2563-7.*
Itani, Synlett (1995), (2), 213.*
Nagao, J. Org. Chem. 1992, vol. 57, 4243-4249.*
Translation of WO 2006/028037 (2006).*
Chinese Office Action together with English translation issued Mar. 17, 2011 in corresponding Chinese Application No. 200780022465.5.
Supplementary European Search Report issued May 3, 2011 in corresponding European Application No. 07 74 5204.
International Preliminary Report on Patentability issued Dec. 31, 2008 including translation of PCT Written Opinion in International (PCT) Application No. PCT/JP2007/061937.
International Search Report issued Aug. 21, 2007 in the International (PCT) Application PCT/JP2007/061937 of which the present application is the U.S. National Stage.
Chinese Office Action issued in Application No. 200780022465.5 dated Sep. 26, 2011 with its English translation.

* cited by examiner

*Primary Examiner* — Mark Berch
(74) *Attorney, Agent, or Firm* — Wenderoth, Lind & Ponack, L.L.P.

(57) ABSTRACT

The present invention relates to a method for crystallization of (2R)-2-{(3S,4S)-3-[(1R)-1-(tert-butyldimethylsilyloxy) ethyl]-2-oxoazetidin-4-yl}propionic acid, and is characterized in that crystallization is carried out by mixing a solution containing the compound with a substituted aromatic hydrocarbon solvent and/or a halogenated hydrocarbon solvent. The method can provide a crystal of the compound with a high purity and a high yield while the content of 2S isomer is kept at a low level.

9 Claims, No Drawings

METHOD FOR CRYSTALLIZATION OF AZETIDINONECARBOXYLIC ACID

TECHNICAL FIELD

The present invention relates to an improved method for crystallization of azetidinonecarboxylic acid useful as a synthesis intermediate of a 1β-methylcarbapenem derivative having an antibacterial activity.

BACKGROUND ART

A 1β-methylcarbapenem derivative has an excellent antibacterial activity to pathogenic bacteria in a wide range including gram positive and gram negative microorganism; has particularly strong antibacterial activity even to cephem-resistant bacteria; and is excellent in stability in a living body. Therefore, the derivative has drawn attention as an antibacterial agent.

Such a 1β-methylcarbapenem derivative is synthesized by various methods. Azetidinonecarboxylic acid represented by the following formula (1):

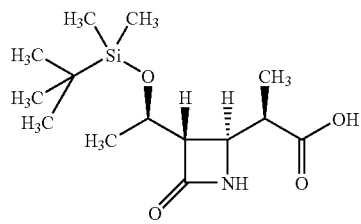

(1)

is known as useful synthesis intermediate for the derivative, and many synthesis methods thereof are disclosed. In a synthesis method of the compound represented by the formula (1) (hereinafter, sometimes referred to as a "compound (1)"), the following methods are known as a method of obtaining crystal thereof:

A) a method of carrying out crystallization in water to obtain the crystal by acidifying an aqueous alkaline solution of the compound (1) with an aqueous hydrochloric acid solution (Patent Documents 1 and 2);

B) a method of acidifying an aqueous alkaline solution of the compound (1) with an aqueous hydrochloric acid solution; carrying out extraction with ethyl acetate; thereafter obtaining a crystalline solid substance by distillation of an ethyl acetate solution of the compound (1), which is obtained by drying with magnesium sulfate and filtration, under reduced pressure; and washing the solid substance with hexane to obtain the crystal (Patent Document 3);

C) a method of acidifying an aqueous alkaline solution of the compound (1) with an aqueous hydrochloric acid solution; carrying out extraction with ethyl acetate; concentrating the ethyl acetate solution of the compound (1), which is obtained by drying with magnesium sulfate and filtration, under reduced pressure; crystallizing from the residue by using an ethyl acetate and hexane solvent to obtain the crystal (Patent Document 4); and D) a method extracting the compound (1) obtained by synthesis reaction with ethyl acetate, dissolving again the residue obtained by drying and concentration process in ethyl acetate, removing insoluble matter by filtration, concentrating the filtrate to obtain a crystalline solid, and re-crystallizing the solid from a mixed solvent of ethyl acetate and benzene to obtain the crystal (Patent Document 5).

However, the methods of obtaining the crystal have the following problems in term of a crystal recovery yield and a crystal purity of the compound (1):

low purity by the methods A) to C) and
low yield by the method D).

All of the above-mentioned methods have problems and thus are not satisfactory as a production method of the compound (1).

Further, as a result of studies by the inventors of the present invention, it was found that the above-mentioned methods A) to C) are inferior in the removal effect of a compound represented by the following formula (2) (hereinafter, sometimes referred to as "2S isomer"):

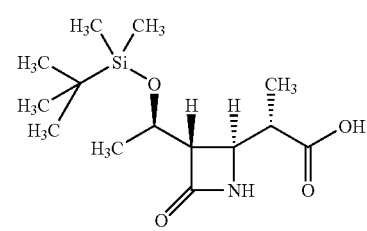

(2)

as a byproduct of the processes. In the synthesis of a precursor needed to produce the compound (1), investigations and researches relevant to a method of controlling byproduct production of a compound to be a precursor of the 2S isomer are positively carried out. The fact can be understood from Patent Documents 2 and 4. The methods A) to C) inferior in the 2S isomer removal effect are insufficient as a method for producing the compound (1) which is an intermediate of a pharmaceutical agent, since suppression of the content of the 2S isomer contained the crystal of the compound (1) are very critical issue.

Furthermore, the above-mentioned methods B) to D) are not satisfactory as a production method of the compound (1), since the methods involve a large number of complicated and non-economical operations from a viewpoint of industrial production scale. The operation is exemplified by drying of the ethyl acetate solution obtained with extraction of the compound (1) by using magnesium sulfate or the like and following filtration needed after the drying, recrystallization of the crystalline solid obtained by repeating concentration and dissolution, and the like.

Patent Document 1: JP 7-25848 A
Patent Document 2: JP 2000-44538 A
Patent Document 3: JP 5-105660 A
Patent Document 4: WO 2002/012230
Patent Document 5: JP 4-368365 A

DISCLOSURE OF THE INVENTION

Problems to be Solved by the Invention

As described above, the conventional methods of obtaining the crystal have the above-mentioned problems in terms of a crystal production yield or a crystal purity, and are not satisfactory as the production method of the compound (1), since the methods are inferior in the effect of removing 2S isomer represented by the formula (2), and involve a large number of complicated and non-economical operations in consideration of industrial scale production.

An objective to be achieved by the present invention is to provide an improved method of crystallization to obtain a crystal of the compound (1) with a high yield and a high purity.

Means for Solving the Problems

The present inventors made intensive studies on the method of crystallization of the compound (1). As a result, the inventors found that the compound represented by the formula (2) can be efficiently removed and a crystal of the compound (1) can be obtained with a high yield and a high purity by mixing a solution containing the compound (1) with a substituted aromatic hydrocarbon solvent and/or a halogenated hydrocarbon solvent and carrying out crystallization; and accordingly the finding leads to completion of the present invention.

The present invention relates to a method for producing a compound represented by the formula (1), characterized in comprising a step of mixing a solution of (2R)-2-{(3S,4S)-3-[(1R)-1-(tert-butyldimethylsilyloxy)ethyl]-2-oxoazetidin-4-yl}propionic acid represented by the formula (1):

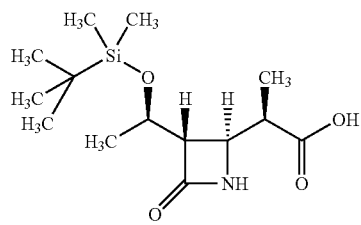

(1)

with a substituted aromatic hydrocarbon solvent and/or a halogenated hydrocarbon solvent for crystallization.

Further, the present invention relates to (2R)-2-{(3S,4S)-3-[(1R)-1-(tert-butyldimethylsilyloxy)ethyl]-2-oxoazetidin-4-yl}propionic acid represented by the general formula (1), wherein a content of (2S)-2-{(3S,4S)-3-[(1R)-1-(tert-butyldimethylsilyloxy)ethyl]-2-oxoazetidin-4-yl}propionic acid represented by the formula (2):

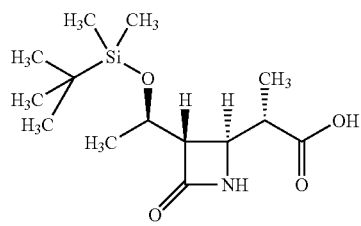

(2)

is 1% or less.

Furthermore, the present invention relates to a crystal of (2R)-2-{(3S,4S)-3-[(1R)-1-(tert-butyldimethylsilyloxy)ethyl]-2-oxoazetidin-4-yl}propionic acid represented by the formula (1), wherein the crystal shows a diffraction intensity peaks at diffraction angles of 7.48°, 11.30°, 14.50°, 15.04°, 15.54°, 16.54°, 16.94°, 18.58°, 22.68°, 24.24°, 28.50° and 31.62° in a powder x-ray diffraction pattern.

Effect of the Invention

The present invention provides an improved method of crystallization of the compound (1) useful as a synthesis intermediate of a 1β-methylcarbapenem derivative, and the intermediate with high purity, and a crystal of the intermediate.

BEST MODE FOR CARRYING OUT THE INVENTION

Hereinafter, the present invention is described in detail.

The present invention is characterized in comprising a step of mixing a solution of (2R)-2-{(3S,4S)-3-[(1R)-1-(tert-butyldimethylsilyloxy)ethyl]-2-oxoazetidin-4-yl}propionic acid represented by the formula (1):

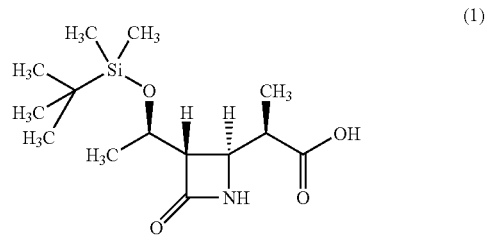

(1)

with a substituted aromatic hydrocarbon solvent and/or a halogenated hydrocarbon solvent for crystallization.

At first, a solution in which the compound (1) is dissolved is described.

A solution in which the compound (1) is dissolved is a solution containing the compound (1) partially or completely dissolved in a good solvent described below (hereinafter, sometimes abbreviated as "good solvent solution of the compound (1)"). A good solvent is a solvent having high solubility of the compound (1), and is described below with a specific example.

An example of a good solvent of the compound (1) may include ethers, nitriles, esters, ketones, alcohols, amides, and the solvent mixtures thereof. Ethers may include tetrahydrofuran, diethyl ether, 1,4-dioxane and methyl tert-butyl ether; nitriles may include acetonitrile and propionitrile; esters may include fatty acid esters such as methyl acetate, ethyl acetate, n-propyl acetate, isopropyl acetate, n-butyl acetate, sec-butyl acetate, isobutyl acetate, tert-butyl acetate, pentyl acetate, methyl propionate and ethyl propionate; ketones may include acetone, 2-butanone, 3-methyl-2-butanone, 2-pentanone, 3-pentanone, 4-methyl-2-pentanone and 2-hexanone; alcohols may include methanol, ethanol, 1-propanol, 2-propanol, n-butanol and 2-butanol; amides may include N,N-dimethylformamide, N,N-dimethylacetamide, N-methylpyrrolidone and N-ethylpyrrolidone.

Among the above solvents, ethers, esters, ketones and alcohols are preferable, and esters and ketones are more preferable. As esters, acetic acid esters such as methyl acetate, ethyl acetate, n-propyl acetate, isopropyl acetate, n-butyl acetate, sec-butyl acetate, isobutyl acetate, tert-butyl acetate and the solvent mixtures thereof are preferable, and ethyl acetate is particularly preferable. As ketones, ketones having 1 to 5 carbon atoms such as acetone, 2-butanone, 3-methyl-2-butanone, 2-pentanone, 3-pentanone, and the solvent mixtures thereof are preferable, and acetone and 2-butanone are particularly preferable.

A good solvent solution of the compound (1) may be a crude reaction solution in which the compound (1) is synthesized by a conventionally known method and a good solvent is contained, or a solution obtained by dissolving the compound (1), which is once isolated, in a good solvent. Further, the solution may be a solution obtained by subjecting a crude reaction solution of the compound (1) to post-treatment such as washing with water optionally containing an acid, a base, a salt or the like, concentration adjustment by condensation, insoluble matter filtration treatment, and adsorption treatment with activated carbon, based on the necessity. Further, the solution may be a homogenous or nonhomogenous solution obtained by concentrating the crude reaction solution in which the compound (1) is synthesized or the good solvent solution containing the compound (1) dissolved therein, or furthermore may be a slurry obtained by carrying out concentration to partially precipitate the compound (1). No need to say, another solvent other than the good solvent may exist to an extent that no bad effect is caused. For example, it is effective and particularly preferable for production in industrial scale to mix water with the good solvent solution of the compound (1) to give a water-containing solution, since a solubility of the compound (1) in the good solvent solution can be improved and a concentration of the compound (1) in the solution can be increased to reduce a volume of the good solvent solution.

A concentration of the compound (1) in a good solvent solution is not particularly limited; however is generally preferably 1% by weight or higher, more preferably 3% by weight or higher, and even more preferably 5% by weight or higher, in consideration of a productivity or the like. Further, an upper limit of the concentration of the compound (1) in the good solvent solution is preferably equal to or lower than a saturated solubility of the compound (1) in a good solvent to be used; however the solution may be supersaturated or may be a slurry by partial precipitation.

Next, a substituted aromatic hydrocarbon solvent and a halogenated hydrocarbon solvent to be used in the present invention is described.

In the present invention, a substituted aromatic hydrocarbon solvent and/or a halogenated hydrocarbon solvent are used as a poor solvent. Hereinafter, the substituted aromatic hydrocarbon solvents and the halogenated hydrocarbon solvents may be collectively called as "a poor solvent" in some cases. The poor solvent means a solvent having a low solubility of the compound (1). It is not common to use the substituted aromatic hydrocarbon solvent and the halogenated hydrocarbon solvent as a poor solvent at a time of crystallizing a common organic compound, since the solvents have a property of well dissolving an organic compound. Even if the solvents can be used as a poor solvent, it is not common to use the substituted aromatic hydrocarbon solvent and the halogenated hydrocarbon solvent as a poor solvent, since the solvents more easily dissolve an organic compound than aliphatic hydrocarbons such as hexane often used as a poor solvent and tend to cause undesirable consequence such as low recovery ratio by crystallization. The present invention is completed on the basis of a finding that the compound (1) with a high yield and a high purity can be obtained by using the substituted aromatic hydrocarbon solvent and/or the halogenated hydrocarbon solvent as a poor solvent in the crystallization of the compound (1). Such a finding is significantly remarkable.

A substituted aromatic hydrocarbon solvent is not particularly limited as long as the solvent is a poor solvent of the compound (1); however includes aromatic hydrocarbons having one or more substituents such as alkyl groups having 1 to 4 carbon atoms, halogens, nitro groups, and solvent mixtures thereof. Naturally, in case that there are two or more substituent groups, ortho-, meta- and para-position isomers may be included. The example of alkyl groups having 1 to 4 carbon atoms includes methyl, ethyl, n-propyl, isopropyl and the like. The example of halogens includes fluorine, chlorine, bromine and iodine. Among the examples, aromatic hydrocarbons having one or more substituents of methyl group and chlorine and the solvent mixtures thereof are preferable; toluene, o-xylene, m-xylene and p-xylene are more preferable; and toluene is particularly preferable.

The above halogenated hydrocarbon solvents are not particularly limited as long as the solvents are a poor solvent of the compound (1); and include chain halogenated hydrocarbon solvents such as dichloromethane, 1,1-dichloroethane, 1,2-dichloroethane, 1,1,1-trichloroethane and the like. Among the example, dichloromethane is preferable.

The above substituted aromatic hydrocarbon solvents and halogenated hydrocarbon solvents may be singly used respectively, or the combination thereof may be used.

Next, a method of crystallization of the compound (1) of the present invention is described.

In the present invention, crystallization is carried out by a method of mixing a good solvent solution of the compound (1) and a poor solvent.

When crystallization is carried out, a poor solvent may be added to a good solvent solution of the compound (1) or a good solvent solution of the compound (1) may be added to a poor solvent. In the case of adding the poor solvent to the good solvent solution of the compound (1), the addition may be carried out at once or stepwise. In the case of adding the good solvent solution of compound (1) to the poor solvent, the addition may be also carried out at once or stepwise. In the case of the stepwise addition, the solvent may be added continuously or the solvent is divided into several portions and the portions may successively be added. Further, at the time of mixing the good solvent solution of compound (1) and the poor solvent, the solution and the solvent may be simultaneously added to be mixed.

Before mixing a good solvent solution of the compound (1) and a poor solvent, the good solvent solution of the compound (1) may be subjected to concentration crystallization or cooling crystallization to crystallize a portion of the compound (1) and then the poor solvent may be mixed as described above. The good solvent solution of the compound (1) formed to be in a slurry state by crystallization and the poor solvent may be mixed to further accelerate crystallization.

In addition, a crystallization method by mixing a good solvent solution of the compound (1) and a poor solvent may also be carried out properly in combination with concentration crystallization or cooling crystallization.

In such a case that a boiling point of a poor solvent is higher than a boiling point of a good solvent to be used for a good solvent solution of the compound (1) or a good solvent and a poor solvent are azeotropic, it is preferable to carry out concentration at the time of mixing the good solvent solution of the compound (1) and the poor solvent and/or after mixing the solution and the solvent, since a ratio of the good solvent in a crystallization solution can efficiently be decreased and a crystal recovery ratio can be improved. When a ratio of a poor solvent is higher in a solvent composition before solid-liquid separation operation described later, the crystal can be obtained at a higher crystal recovery ratio.

A method involving a crystallization method of mixing a good solvent solution of the compound (1) and a poor solvent in combination with a concentration crystallization and further in combination with cooling crystallization is particularly preferable, since the method can further improve a crystal recovery ratio. No need to say, when the concentration crystallization and the cooling crystallization are carried out, either one operation may be carried out previously and both operations may be repeated any times.

Thus, a crystal with a high purity can be obtained by any crystallization method described above.

In the above crystallization operations, a seed crystal may be added if necessary. A use amount of the seed crystal is not particularly limited; however, a lower limit is preferably not less than 0.001 w/w times, more preferably not less than 0.003 w/w times, and particularly more preferably not less than 0.005 w/w times, respective to the compound (1) in a good solvent solution. An upper limit of the compound (1) in a good solvent solution is preferably not more than 0.2 w/w times, more preferably not more than 0.1 w/w times, and further more preferably not more than 0.05 w/w times, respective to the compound (1) in a good solvent solution.

In the crystallization by mixing a good solvent solution of the compound (1) and a poor solvent and/or concentration crystallization, a temperature is not particularly limited; however, the temperature is preferably 50° C. or lower, more preferably 40° C. or lower, and particularly more preferably 30° C. or lower, since the compound (1) is sometimes inferior in a heat stability.

A use amount of a poor solvent is preferably set every time in accordance with a crystallization method in order to obtain a desired crystallization recovery ratio. The amount is not particularly limited; however, a weight ratio of the poor solvent in a composition of solvent contained in a mother liquid is generally ½ or higher, preferably ⅔ or higher, and more preferably ¾ or higher. The crystallization mother liquid means a liquid phase part immediately before a solid-liquid separation operation described later after a crystallization method of mixing a good solvent solution of the compound (1) and a poor solvent or after an operation of concentration crystallization and/or cooling crystallization to be carried out on the basis of necessity. An formula for calculating a weight ratio of a poor solvent contained in the mother liquid is defined as ([weight of poor solvent])/([weight of good solvent])+[weight of poor solvent]).

In a crystallization method of mixing a good solvent solution of the compound (1) and a poor solvent, the poor solvent may be used in a manner that a weight ratio of the poor solvent can satisfy the above-mentioned ratio. In case that a crystallization method of mixing a good solvent solution of the compound (1) and a poor solvent is combined with a concentration crystallization to be carried out, a mixing of the good solvent solution of the compound (1) and the poor solvent and concentration may be carried out in a manner that a weight ratio of the poor solvent contained in the mother liquid can satisfy the above ratio.

In the present invention, aging may be carried out at the last of a crystallization. An aging temperature is not particularly limited; however, the temperature is preferably as low as possible in terms of increase of a crystallization recovery ratio and is generally 20° C. or lower, preferably 10° C. or lower, and more preferably 0° C. or lower. An aging time is not particularly limited; however, a lower limit is generally 10 minutes or longer, preferably 30 minutes or longer, and more preferably 1 hour or longer. An upper limit is generally 30 hours or shorter, preferably 20 hours or shorter, and more preferably 10 hours or shorter, in consideration of a productivity.

Generally, the above crystallization by mixing a good solvent solution of the compound (1) and a poor solvent, concentration crystallization, cooling crystallization and aging are carried out with stirring. An intensity of the stirring is not particularly limited; however, the intensity is preferably not lower than 10 w/m$^3$, more preferably not lower than 50 w/m$^3$, furthermore preferably not lower than 100 w/m$^3$, and even more preferably not lower than 300 w/m$^3$, as needed motive energy of stirring per unit volume.

A crystal of the compound (1) obtained by the crystallization method of the present invention can be isolated by common solid-liquid separation operation.

According to the crystallization method of the present invention, it is possible to obtain the highly pure compound (1) with a high crystal recovery ratio by executing crystallization in industrially simple operation such as mixing and concentration of a good solvent solution of the compound (1) which is obtained by post-treatment such as extraction operation of a crude reaction solution, without carrying out complicated operation, which is disclosed as a conventional crystal obtaining method, such as drying of a solution containing the compound (1) and recrystallization. The crystallization method of the present invention is particularly useful at the time of production of the compound (1) in an industrial scale, since the method is simple in an operation and economical due to an improvement of a productivity.

In the case of the methods as the above Patent Documents, a precursor of a compound represented by the following formula (2):

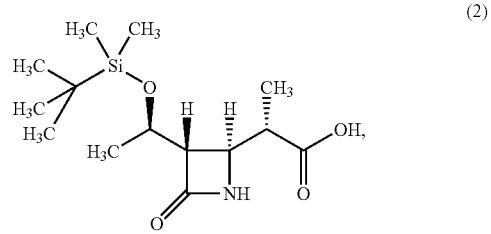

which is an isomer of the compound (1), (hereinafter, sometimes referred to as a "2S isomer") is often produced as a byproduct at the time of synthesizing a precursor of the compound (1), and the 2S isomer is contained in a good solvent solution of the compound (1) at the time of synthesizing the compound (1) from the precursor of the compound (1). However, the compound (1) can be obtained with high yield and high purity and the 2S isomer can be effectively removed by the crystallization method of the invention.

When the crystallization method of the present invention is employed, the 2S isomer as an impurity can be removed at 50% or higher of a removal ratio, preferably 60% or higher, and more preferably 65% or higher; and thus, the crystallization method of the present invention is very useful in terms of a remarkable decrease of a content of a 2S isomer contained in a crystal of the compound (1). The formula for calculating the removal ratio can be defined as ([content of 2S isomer to compound (1) in good solvent solution]−[content of 2S isomer in crystal])/[content of 2S isomer to compound (1) in good solvent solution]×100(%).

The compound (1) thus obtained in the above-mentioned manner is a compound with high purity having a content of the 2S isomer as an impurity of 1% or less, preferably 0.5% or less, and more preferably 0.3% or less. Since a content of an isomer contained in a 1β-methylcarbapenem antibiotic synthesized as a pharmaceutical agent from the compound (1) can be decreased by decreasing a content of the 2S isomer remaining in a crystal, the compound (1) with an extremely small content of the 2S isomer is very useful.

The compound (1) obtained by using the present invention is remarkably useful as a synthesis intermediate for producing a 1β-methylcarbapenem derivative with a high purity.

The crystal of the compound (1) obtained in the above-mentioned manner shows main peaks at diffraction angles of, for example, 2θ=7.48°, 11.30°, 14.50°, 15.04°, 15.54°, 16.54°, 16.94°, 18.58°, 22.68°, 24.24°, 28.50° and 31.62° in a powder x-ray diffraction obtained by irradiating Kα-beam of Cu, having a wavelength of λ=1.54 Å. The main peaks are peaks with 10 or higher relative intensity in case that an intensity of a peak at a diffraction angle of 2θ=15.04° is defined to be 100. When a crystal is represented by employing a diffraction angle 2θ in the present specification, a value of a diffraction angle 2θ is not limited to values at which the above-mentioned peaks exist and ranges thereof, and may include a margin of errors. A range within which such errors are generated can be easily expected by a person skilled in the art from a measurement condition and the like; and such a range of errors may be, for example, ±0.05°. The obtained crystal is easily handled and thus useful.

EXAMPLES

Hereinafter, the present invention is described much more in detail with reference to Examples, Comparative Examples and Reference Examples; however it is not intended that the present invention be limited to the Examples.

Reference Example 1

Production of good solvent solution of (2R)-2-{(3S,4S)-3-[(1R)-1-(tert-butyldimethylsilyloxy)ethyl]-2-oxoazetidin-4-yl}propionic acid (compound (1))

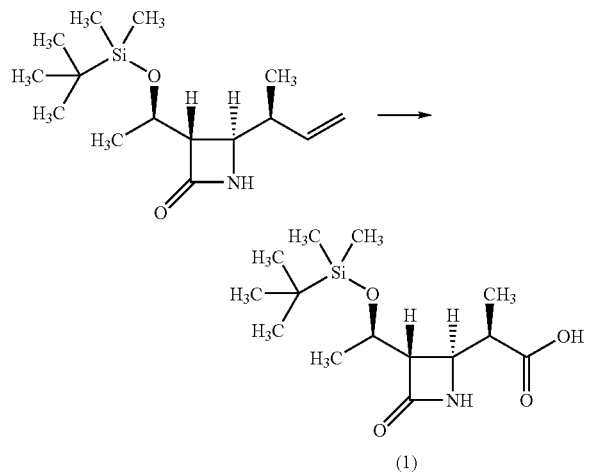

After (3S,4R)-3-[(1R)-1-(tert-butyldimethylsilyloxy)ethyl]-4-[(1S)-1-methyl-2-propenyl]azetidin-2-one (10.6 g), acetic acid (17.1 g), ethyl acetate (105 ml) and water (73 ml) were mixed, the mixture was stirred. To the mixture, potassium permanganate (30.0 g) was added over 1.5 hours while the reaction solution temperature was kept at 6 to 15° C. Then, the reaction solution was stirred at 7° C. for 3 hours. Thereafter, a 27% aqueous solution of sodium hydrogen sulfite (157 ml) was added while the reaction solution temperature was kept at 6 to 13° C., and the solution was stirred at 7° C. for 30 minutes. Further, 6N HCl was added to adjust pH of the reaction solution to be at 1.4, and the reaction solution was stirred at 7° C. for 30 minutes. After an organic layer obtained by separating the resulting reaction solution was washed with water (55 ml) twice, ethyl acetate (28 ml) was added to obtain an ethyl acetate solution (112.5 g) containing 10.2 g of (2R)-2-{(3S,4S)-3-[(1R)-1-(tert-butyldimethylsilyloxy)ethyl]-2-oxoazetidin-4-yl}propionic acid. The solution contained a 2S isomer in an amount of 2.0% on the basis of the compound (1).

Example 1

The ethyl acetate solution (40.0 g) of the compound (1) obtained in Reference Example 1 was concentrated to 10.0 g while the inner temperature was kept at 24 to 30° C. As a result, a crystal was precipitated. While the obtained slurry was stirred, toluene (17.8 g) was added. The slurry was further concentrated to 8.2 g, while the inner temperature was kept at 21 to 30° C. After toluene (41.9 g) was added, the slurry was cooled to −20° C. and stirred for 1.5 hours. It was confirmed that the weight ratio of toluene in the composition of the solvents at the moment was ½ or higher. After the crystal was separated by filtration, the crystal was washed with toluene (4.2 g). The obtained wet crystal was dried under reduced pressure at room temperature for 24 hours to obtain 3.4 g of a dry crystal of the compound (1).

Crystal purity: 99.0%
2S Isomer content: 0.7%
2S Isomer removal ratio: 67%
Crystal recovery ratio: 92.1%

Comparative Example 1

The ethyl acetate solution (40.0 g) of the compound (1) obtained in Reference Example 1 was concentrated to 7.8 g while the inner temperature was kept at 24 to 30° C. As a result, a crystal was precipitated. While the obtained slurry was stirred, ethyl acetate (22.8 g) was added. The slurry was further concentrated to 7.8 g, while the inner temperature was kept at 27 to 30° C. After ethyl acetate (10.6 g) was added, the obtained slurry was cooled to −50° C. and stirred for 1.5 hours. After the crystal was separated by filtration, the crystal was washed with ethyl acetate (3.6 g), and the obtained wet crystal was dried under reduced pressure at room temperature for 27 hours to obtain 3.2 g of a dry crystal of the compound (1).

Crystal purity: 98.4%
2S Isomer content: 1.2%
2S Isomer removal ratio: 36%
Crystal recovery ratio: 88.5%

Reference Example 2

Production of aqueous alkaline solution of (2R)-2-{(3S,4S)-3-[(1R)-1-(tert-butyldimethylsilyloxy)ethyl]-2-oxoazetidin-4-yl}propionic acid (compound (1))

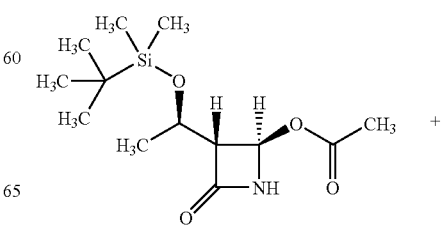

-continued

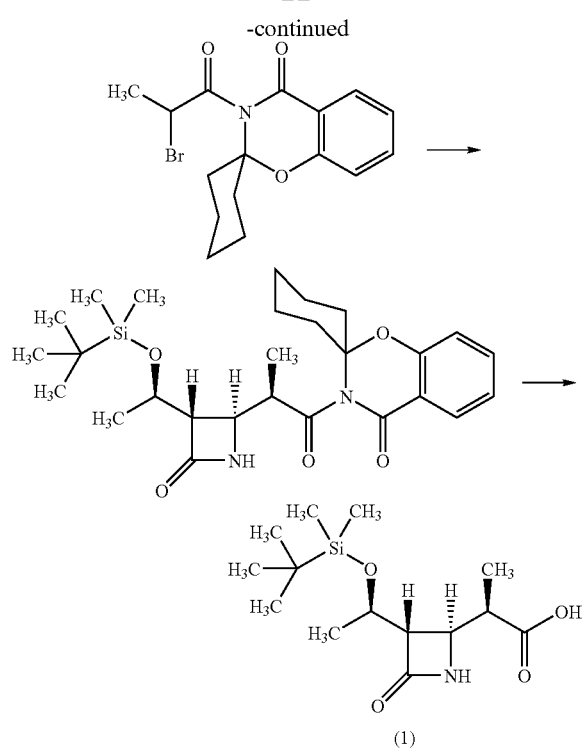

(1)

After zinc metal (6.8 g) of which surface was treated with diluted hydrochloric acid and 3-(2-bromopropanoyl)-spiro[3-azachloman-2,1'-cyclohexan]-4-one (1.8 g) were added to dry tetrahydrofuran (60 ml), the mixture was stirred at 25° C. for 1.7 hours. After a solution obtained by dissolving 3-(2-bromopropanoyl)-spiro[3-azachloman-2,1'-cyclohexan]-4-one (16.5 g) and (3R,4R)-4-acetoxy-3-[(1R)-1-tert-butyldimethylsilyl oxy]-2-azetizinone (10.0 g) in dry tetrahydrofuran (50 ml) was added at the same temperature over 30 minutes to the mixture, the resulting mixture was stirred for 15 hours. Thereafter, the solution was concentrated until the amount was decreased to 50 ml, while the inner temperature was kept at about 20° C. The unreacted zinc component was separated by filtration. After the filtrate was diluted with toluene (70 ml), water (30 ml) was added under cooling with ice, and a 1 N aqueous solution of hydrochloric acid was further added to adjust pH at 4.0. The organic layer obtained by solution separation was washed with water (15 ml) twice. While the inner temperature was kept at 20 to 30° C., the solvent was removed by distillation to obtain 30.0 g of a toluene solution containing 15.5 g of 3-{(2R)-2-{(3S,4R)-3-[(1R)-1-tert-butyldimethylsilyloxy ethyl]-2-oxoazetidin-4-yl}propionyl}-spiro[2,3-dihydro-4H-1,3-benzoxadine-2,1'-cyclohexan]-4-one.

After methanol (150 ml) was added for dissolution in the obtained toluene solution, the solution was cooled to 0° C. Then, 30% aqueous hydrogen peroxide (11.8 ml) and a 15% aqueous solution of sodium hydroxide (15.3 g) were successively added to the solution. The mixture was stirred at the same temperature for 1 hour and 40 minutes. Next, after a 10% aqueous solution of sodium sulfite (145 g) was added dropwise over 1 hour and 20 minutes, the mixture was stirred for 30 minutes. A 1 N aqueous solution of hydrochloric acid was added to adjust pH at 9.6, and methanol was removed by vacuum distillation. The precipitated crystal component was separated by filtration and the crystal component was washed with water (50 ml) twice. The filtrate and the washing solution was mixed to obtain an aqueous alkaline solution containing 8.9 g of (2R)-2-{(3S,4S)-3-[(1R)-1-(tert-butyldimethylsilyloxy)ethyl]-2-oxoazetidin-4-yl}propionic acid. The solution contained the 2S isomer in an amount of 2.7% on the basis of the compound (1).

Reference Example 3

Production of good solvent solution of (2R)-2-{(3S,4S)-3-[(1R)-1-(tert-butyldimethylsilyloxy)ethyl]-2-oxoazetidin-4-yl}propionic acid (compound (1))

After ethyl acetate (75 ml) was added to the aqueous alkaline solution containing 4.5 g of (2R)-2-{(3S,4S)-3-[(1R)-1-(tert-butyldimethylsilyloxy)ethyl]-2-oxoazetidin-4-yl}propionic acid (compound (1)) obtained in Reference Example 2, 6N HCl was added under cooling with ice to adjust pH at 2.9. After the mixture was stirred for 10 minutes, an organic layer obtained by separating a water layer was washed with water (15 ml) twice to obtain an ethyl acetate solution containing 4.4 g of (2R)-2-{(3S,4S)-3-[(1R)-1-(tert-butyldimethylsilyloxy)ethyl]-2-oxoazetidin-4-yl}propionic acid. The solution contained the 2S isomer in an amount of 2.7% on the basis of the compound (1).

Example 2

To the ethyl acetate solution of the compound (1) obtained in Reference Example 3, toluene (150 ml) was added over 10 minutes. As a result, a crystal was precipitated. The obtained slurry was concentrated to 29.3 g, while the inner temperature was kept at 20 to 30° C. The obtained slurry was cooled to −20° C. and stirred at the same temperature for 2.5 hours. It was confirmed that the weight ratio of toluene in the composition of the solvents at the moment was ½ or higher. After the crystal was separated by filtration, the crystal was washed with toluene (8 ml) twice. The obtained wet crystal was dried under reduced pressure at room temperature for 24 hours to obtain 4.3 g of a dry crystal of the compound (1).

Crystal purity: 98.7%

2S Isomer content: 0.8%

2S Isomer removal ratio: 70%

Crystal recovery ratio: 97.5%

Comparative Example 2

Concentrated hydrochloric acid was added to the aqueous alkaline solution containing 4.4 g of the compound (1) obtained in Reference Example 2 under cooling with ice to adjust pH at 3.0. As a result, a crystal was precipitated. The obtained slurry was stirred for further 30 minutes under cooling with ice. The crystal was separated by filtration, and washed with water (25 ml). The obtained wet crystal was dried under reduced pressure at room temperature for 17 hours to obtain 4.7 g of a crystalline solid of the compound (1), containing 4.3 g of pure compound.

Crystal purity: 90.6%

2S Isomer content: 2.2%

2S Isomer removal ratio: 18%

Crystal recovery ratio: 96.7%

Reference Example 4

Production of good solvent solution of (2R)-2-{(3S, 4S)-3-[(1R)-1-(tert-butyldimethylsilyloxy)ethyl]-2-oxoazetidin-4-yl}propionic acid (compound (1))

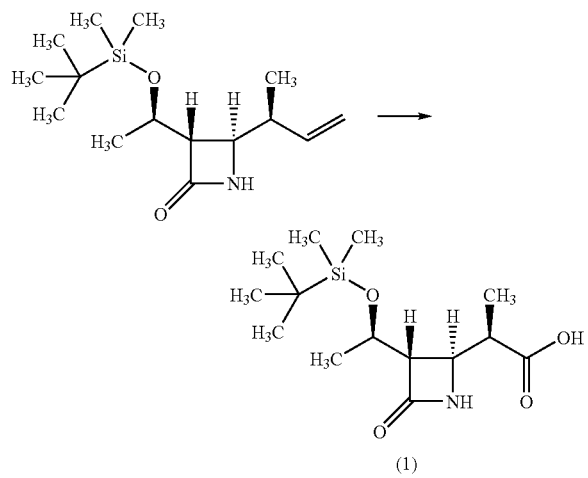

(1)

After (3S,4R)-3-[(1R)-1-(tert-butyldimethylsilyloxy) ethyl]-4-[(1S)-1-methyl-2-propenyl]azetidin-2-one (10.0 g), acetic acid (16.1 g), ethyl acetate (100 ml) and water (70 ml) were mixed, and the mixture was stirred. While the reaction solution temperature was kept at 6 to 15° C., potassium permanganate (28.3 g) was added over 1.5 hours. The mixture was stirred at 7° C. for 3 hours. Thereafter, a 27% aqueous solution of sodium hydrogen sulfite (150 ml) was added, while the reaction solution temperature was kept at 6 to 13° C. The mixture was stirred at 7° C. for 30 minutes, and 6N HCl was further added to adjust pH of the reaction solution to be at 1.5. The mixture was stirred at 7° C. for 30 minutes. An organic layer obtained by separating the mixture was washed with water (50 ml) twice to obtain an ethyl acetate solution containing 9.6 g of (2R)-2-{(3S,4S)-3-[(1R)-1-(tert-butyldimethylsilyloxy)ethyl]-2-oxoazetidin-4-yl}propionic acid. The solution contained a 2S isomer in an amount of 1.3% on the basis of the compound (1).

Example 3

To the ethyl acetate solution containing 4.8 g of the compound (1) obtained in Reference Example 4, toluene (150 ml) was added over 10 minutes. As a result, a crystal was precipitated. The obtained slurry was concentrated to 32.0 g, while the inner temperature was kept at 20 to 30° C. The obtained slurry was cooled to −20° C. and stirred at the same temperature for 2.5 hours. It was confirmed that the weight ratio of toluene in the composition of the solvents at the moment was ¾ or higher. After the crystal was separated by filtration, the crystal was washed with toluene (8 ml) twice, and the obtained wet crystal was dried under reduced pressure at room temperature for 24 hours to obtain 4.7 g of a dry crystal of the compound (1).

Crystal purity: 99.0%
2S Isomer content: 0.3%
2S Isomer removal ratio: 73%
Crystal recovery ratio: 97.5%

Example 4

The powder x-ray diffraction of the crystal obtained by the method of Example 2 was measured by using the following apparatus under the following measurement conditions.

Apparatus:
Rotary twine cathode type x-ray diffraction apparatus Geiger Flex RAD-rA, manufactured by Rigaku Corporation Measurement Conditions:
Used x-ray: Cu—Kα ray; X-ray intensity: 40 kV, 100 mA; Angle range: 2θ=3 to 80°; Scanning speed: 2°/min; Sampling interval: 0.02 seconds; Divergence slit: 1.0°; Receiving slit: 0.6°; Scattering slit: 1.0°

The results are shown in Table 1.

TABLE 1

| Diffraction angle (°) | Relative intensity |
|---|---|
| 7.48 | 66 |
| 11.30 | 58 |
| 14.50 | 38 |
| 15.04 | 100 |
| 15.54 | 14 |
| 16.54 | 10 |
| 16.94 | 16 |
| 18.58 | 28 |
| 22.68 | 38 |
| 24.24 | 14 |
| 28.50 | 12 |
| 31.62 | 16 |

The invention claimed is:

1. A method for crystallizing a compound represented by the formula (1),
comprising a step of mixing a solution prepared by dissolving (2R)-2-{(3S,4S)-3-[(1R)-1-(tert-butyldimethylsilyloxy)ethyl]-2-oxoazetidin-4-yl}propionic acid represented by the following formula (1):

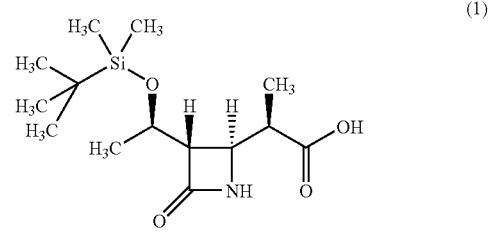

(1)

in a first solvent, with a second solvent which is a solvent consisting essentially of substituted aromatic hydrocarbons and/or a solvent consisting essentially of halogenated hydrocarbons to crystallize the compound of formula (1),
with the proviso that the method is carried out without adding an acid.

2. The method according to claim 1, wherein concentration is carried out during and/or after mixing the solution of the compound represented by the formula (1) with the second solvent.

3. The method according to claim 1, wherein a ratio of a total weight of the second solvent to the total weight of the first and second solvents is ½ or higher .

4. The method according to claim 1, wherein a temperature of the mixture of the solution of the compound represented by the formula (1) and the second solvent is 50° C. or lower when the crystallization is carried out.

5. The method according to claim 1, wherein the solution of the compound represented by the formula (1) contains an ester or ketone.

6. The method according to claim 1, wherein the solution of the compound represented by the formula (1) contains water.

7. The method according to claim 1, wherein the solution of the compound represented by the formula (1) has a concentration of the compound represented by the formula (1) of 1% by weight or higher.

8. The method according to claim 1, wherein the halogenated hydrocarbon solvent is a non-ring halogenated hydrocarbon.

9. The method according to claim 2, wherein a ratio of a total weight of the second solvent to the total weight of the first and second solvents after carrying out the concentration is ½ or higher.

* * * * *